United States Patent [19]
Moseley

[11] Patent Number: 5,117,461
[45] Date of Patent: May 26, 1992

[54] ELECTROACOUSTIC DEVICE FOR HEARING NEEDS INCLUDING NOISE CANCELLATION

[75] Inventor: William T. Moseley, Shreveport, La.

[73] Assignee: MNC, Inc., Shreveport, La.

[21] Appl. No.: 532,323

[22] Filed: Jul. 10, 1990

Related U.S. Application Data

[63] Continuation-in-part of Ser. No. 392,264, Aug. 10, 1989, abandoned.

[51] Int. Cl.$^5$ .............................................. A61F 11/02
[52] U.S. Cl. ..................................... 381/72; 381/163; 381/71
[58] Field of Search ................... 381/72, 71, 163, 150

[56] References Cited

U.S. PATENT DOCUMENTS

| | | | |
|---|---|---|---|
| 2,972,018 | 2/1961 | Hawley et al. | 381/72 |
| 3,952,158 | 4/1976 | Kyle et al. | 381/72 |
| 4,928,311 | 5/1990 | Trompler | 381/72 |
| 4,972,491 | 11/1990 | Wilcox, Jr. | 381/72 |
| 5,001,763 | 3/1991 | Moseley | 381/71 |

FOREIGN PATENT DOCUMENTS

WO89/12432  12/1989  PCT Int'l Appl. .................. 381/72

Primary Examiner—Forester W. Isen
Attorney, Agent, or Firm—Cushman, Darby & Cushman

[57] ABSTRACT

A device for performing electroacoustic functions including noise cancellation, hearing aid, communication interface, headset, feed for recording device, and headphone functions. The device includes composite transducers connected to a control unit. The composite transducers can be mounted on a headband and are configured to include input transducers for converting acoustic waves into electrical signals for processing by a control unit, and output transducers for converting the processed electrical signals to processed sound waves. The control unit includes an inverter/amplifier and a mixer/output amplifier for inverting the electrical input and controlling the gain for either adjusting the gain to maximize a noise cancellation function or increasing the gain beyond the minimum level heard by the ear to a desired level for a hearing aid function. Connectors for connecting recorders and a boom microphone, and function selection switches are provided by the control means for connecting circuit components of the control unit selectively for performing the above functions. The input and output transducers have oppositely oriented diaphragms mounted in a common plane to provide an inverted acoustic wave in real time for combining with and substantially cancelling an incoming acoustic wave. In this embodiment, an isolation wall means may also be incorporated to prevent sound from the output transducer from propagating back into the input transducer. In a second embodiment, the input and output transducer are both oriented in the same direction toward the user's ear canal.

2 Claims, 6 Drawing Sheets

TOP VIEW

ELECTROACOUSTIC DEVICE FOR HEARING NEEDS INCLUDING NOISE CANCELLATION

This invention relates to electroacoustic devices and more particularly to an improved electroacoustic apparatus which provides useful tools for the human ear and its hearing needs including audio noise cancellation, sound level amplification, and interfaces for communication devices. This is a continuation-in-part of Application Ser. No. 07/392,264, filed Aug. 10, 1989, now abandoned.

BACKGROUND OF THE INVENTION

Electroacoustic devices have included electronic audio noise cancelling devices for the attenuation of broadband noise at the ear. Such devices are either passive devices or active devices. Passive devices have generally comprised rigid cups lined with acoustically absorbent material. The cups are edged with cushions to enclose the ears in substantially air tight cavities lined with the acoustically absorbent material.

Active devices for noise cancellation have included: microphones, amplifiers and loud speakers to measure noises in local areas relatively distant from the sources and to produce equal amplitude and opposite phase acoustic signals to cancel out the sound in the areas. Such known arrangements are prone to produce interference patterns which even increase the noise intensity in other locations.

In one noise cancelling apparatus an array of independent sound cancellation units is arranged over a vibrating noise generating surface. Each unit includes an arrangement of acoustic transducers positioned adjacent the surface to obtain an electrical average of the local acoustic noise generated by a predetermined zone of the surface. The electrical sum average is changed in phase and gain by an active filter whose output drives an acoustic projector also positioned adjacent the surface. The acoustic output sums with the original noise signal in the acoustic far field, thus tending to cancel the noise. In essence, each vibrating surface zone and its associated sound cancellation unit tend to form an acoustic doublet. A signal indicative of the projector output is used as a feedback signal, with appropriate time delays to cancel the effect of the projected output signal being picked up by the unit's transducer, and to cancel the effect of the output of other projectors of the array. Those persons skilled in the art desiring more information concerning this system are referred to U.S. Pat. No. 4,025,724 issued May 24, 1977 to Davidson, Jr. et al.

In another electronic audio noise cancelling device, a microphone is disposed on the outside of an earphone relative to the auditory canal within an ear. An amplifier processing circuit has an input connected to the operational amplifier microphone. The circuit includes a filter channel and an operational amplifier channel. The filter channel includes an active filter and a variable gain amplifier and the operational amplifier channel includes an operational amplifier and a variable gain amplifier. The two variable gain amplifiers are complementary.

The two channels are combined with the summed signal being fed through a user adjustable variable gain amplifier to a summing circuit At the summing circuit a signal on a communication channel is introduced. The summing circuit output is fed to the earphone 12. The amplifier processing circuitry provides for user adjustment of phase and amplification to enable a preferred cancellation signal to be developed to the earphone. The output provides unwanted noise cancellation at the earphone. Those persons having a need for more information concerning the device are referred to UK Patent Application GB 2172769A, published Sept. 24, 1986 for an Ear Defender.

The problems with the above devices stem from acoustic time delay and the use of active filters. In acoustic time delay the distance between the microphone and loudspeaker has a phase shift associated with it; thereby allowing only certain frequencies to be 180 degrees out of phase. In an active filter also, only some frequencies can be made 180 degrees out of phase. Signals that are out of phase by 180 degrees will cancel, but the addition of the phase response of the filter makes for a random response depending on the setting of the filter and the distance between the microphone and loud speaker. An additional problem with the arrangement having a loud speaker downstream of the microphone is that if the speed of sound changes, the frequencies being cancelled also change. Another problem also exists when the microphone is separated from the loud speaker in that a path is created for reflections to enter the ear that are not processed.

Miniature portable sound amplifiers for persons with impaired hearing are well known as hearing aids. A hearing aid includes a microphone, audio amplifier, earphone, and batteries.

SUMMARY OF THE INVENTION

In accordance with the present invention, an apparatus is provided with features as follows:

1. The apparatus reduces the sound level to the ear for improved audible noise reduction;

2. The apparatus is capable of performing a hearing aid function such as amplifying the sound level to the ear;

3. The apparatus provides a communication interface for inputting special signals such as dispatched or emergency communications and providing a signal output from a boom microphone;

4. The apparatus provides an amplified headset which can be used with personal entertainment equipment or where other amplified signals are required to drive a miniature type headset;

5. The apparatus provides a signal source to feed personal or professional recording devices such as mono or binaural microphone sources; and 6. The apparatus provides a normal open air ultralight headphone for use in anyway that this type of headphone may normally be used.

Accordingly it is an object of the present invention to provide an electroacoustic apparatus having improved capabilities to meet the needs of human ears.

Another object of the invention is to provide a multifunction electroacoustic apparatus configured to reduce substantially the circuitry required to perform its functions.

Yet another object of the invention is to provide a multifunction electroacoustic apparatus that minimizes the effect of temperature, humidity, and barometric pressure which change the speed of sound and would change the acoustic time delay and the frequencies that would have been out of phase 180 degrees.

Still another object of the invention is to provide a multifunction electroacoustic apparatus which may receive an acoustic signal and output a processed acoustic signal in the same time domain.

A further object of the invention is to provide a multifunction electroacoustic apparatus having many applications including: noise reduction; noise reduction accompanied by an auxiliary input, and interfacing user circuits connected thereto via access points.

Briefly stated the multifunction electroacoustic apparatus, which constitutes the subject matter of the invention hereinafter described in detail, includes a control unit and at least one composite transducer which might be attached to a headband and connected to the control unit. The control unit provides function selection and the signal processing for the selected function.

The control unit is made small enough to fit into a pocket, worn on a belt, clipped to an apparel suitable to support the unit, or made to fit a variety of other size chassis.

Each composite transducer includes two independent electroacoustic transducers. Depending on the application, the first may be an input transducer for converting sound waves to electric waves and the second may be an output transducer for converting audio frequency electric waves acoustic waves. The transducers are thus mounted so that their diaphragms are oriented in opposite directions, with one transducer mounted in the middle of the other, and with both diaphragms aligned in the same plane. In other applications, hereinafter described, the above mentioned output transducer may be used as an input transducer and if the above mentioned input transducer is a piezoelectric device it may be used as an output device. The composite transducer is encased in an open cell foam to provide: comfort to the person wearing the device, a windscreen for the input transducer, a spacer between the composite transducer and the ear of the person wearing the device for admitting the noise waves directly into the mixing chamber (ear canal), and an absorber for high frequency attenuation.

The open cell foam allows the original acoustic signal to reach the ear by centering the composite transducer over the ear canal so that the original acoustic wave is not blocked entirely. Thus, this same acoustic wave front is received by the input transducer, converted to an electrical signal and processed in the control unit. The processed signal is phase inverted and applied to the output transducer. Since the diaphragms of the input and output transducers are in the same plane, the processed signal output is substantially in the same time domain as the original acoustic wave. That is the original signal and the processed signal are substantially 180 degrees out of phase and cancel in the ear canal. A person skilled in the art will recognize that although the diaphragms of the input and output transducers are in the same plane they both will have independent ballistic characteristics that cause a slight distortion and time delay however, the processed signal output is substantially in the same time domain as the original acoustic wave. Also a very slight delay off the electronics to process the signal exist but again, compared to the speed of sound this is very slight. The high frequency attenuation provided by the open cell foam helps to passively reduce some of the acoustic signal level thereby increasing the efficiency of the apparatus.

BRIEF DESCRIPTION OF THE DRAWINGS

Other features and objects of the invention will become more readily apparent from the following detailed description when read in conjunction with the accompanying drawings in which.

BRIEF DESCRIPTION OF THE PREFERRED EMBODIMENT

Figure 1:
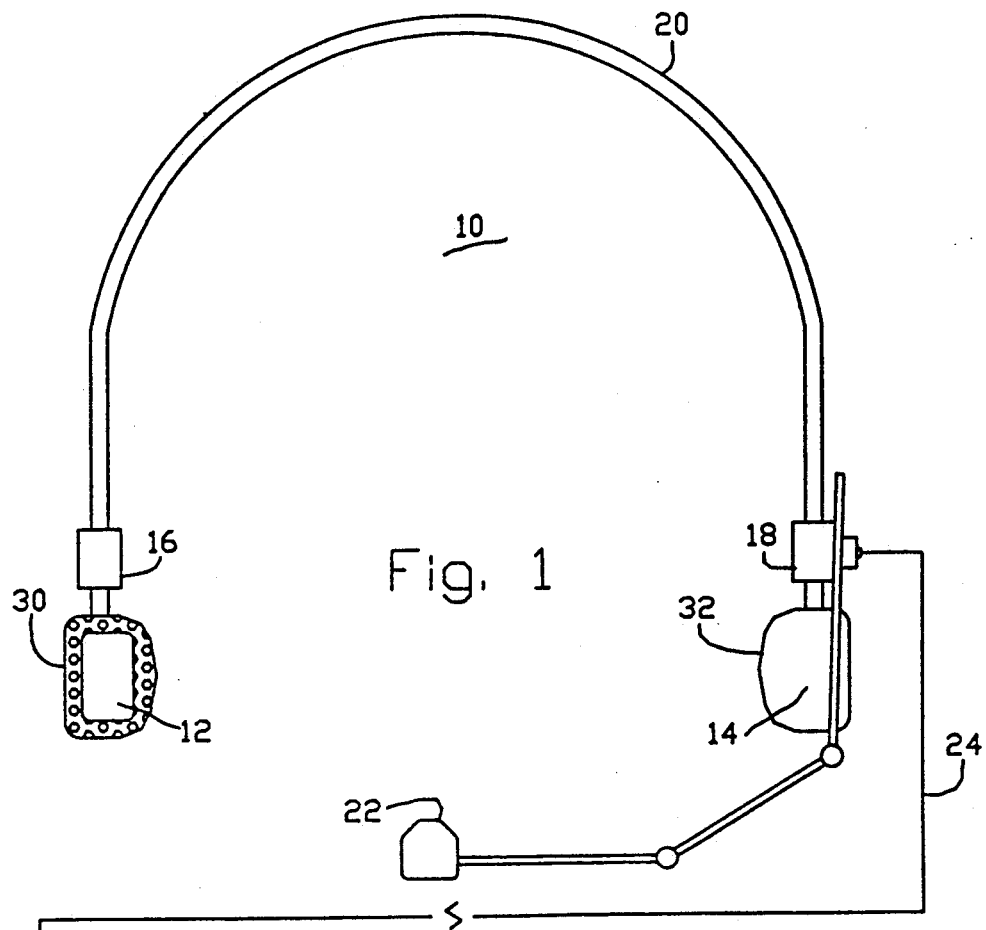
FIG. 1 is a plan view of the multifunction electroacoustic apparatus constituting the subject matter invention.
Figure 3C:
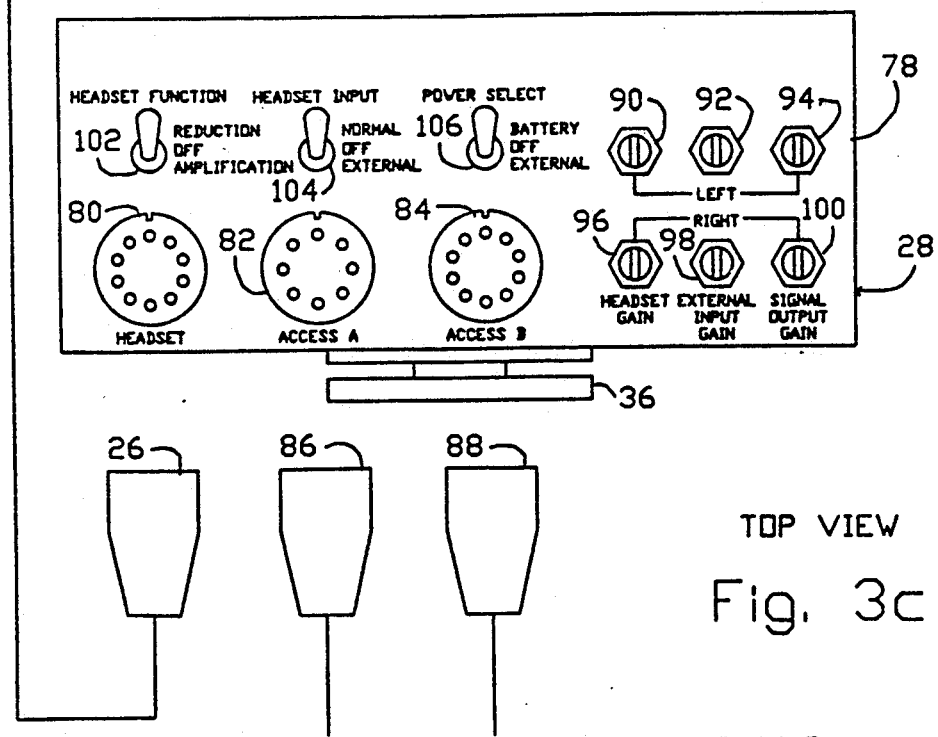
FIGS. 3a-3c are rear, front and top views of the controller.
Figure 3B:
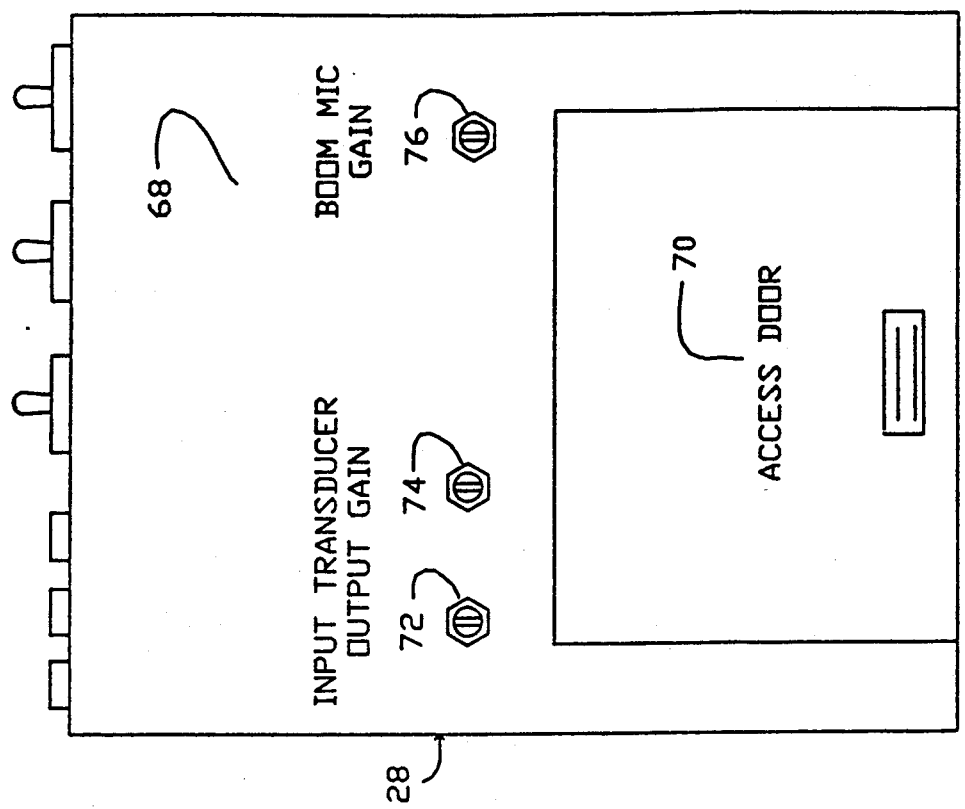
Figure 3A:
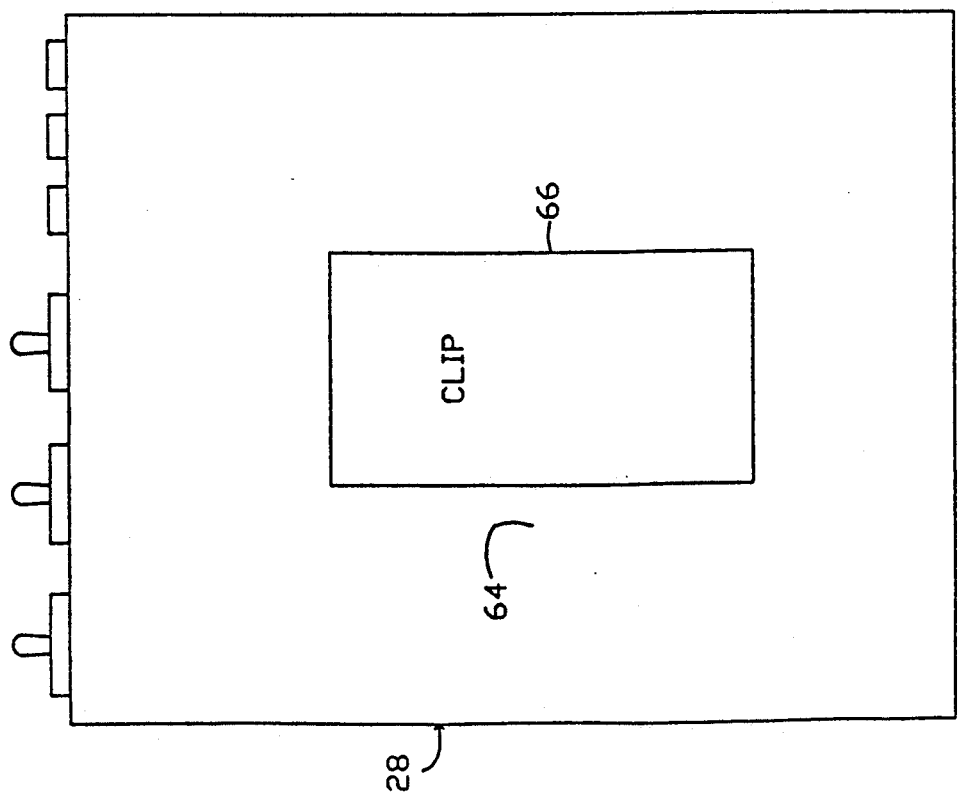

The electroacoustic apparatus 10 (FIG. 1) includes by way of example and not limitation a pair of composite transducer packages 12 and 14 connected to a corresponding pair of attachment blocks 16 and 18 of an adjustable headband 20. Attachment block 18 also attaches a boom microphone 22 to the headband 20. A cable 24 has one end connected to the adjustable headset's composite transducers and connecting the headset to a controller 28 (FIGS. 3a-3c).

The composite transducers 12 and 14 (FIG. 1) are used to convert the acoustic source signal to an electrical signal and simultaneously convert a processed electrical signal to an acoustic signal. They are encased in blocks of open cell foam material 30 and 32. The composite transducers are designed to be held in place directly over the ear canals by the open cell foam blocks. Thus, the composite transducers do not "plug" the ear, as it is necessary to allow the original sound wave to arrive at the ear canal. The open cell foam blocks 30 and 32 are configured to provide: comfort to the person wearing the apparatus, a windscreen for the composite transducers, a spacer between the composite transducers and the ears of the person wearing the device, and high frequency attenuation. Thus configured, the open cell foam blocks allow the original acoustic signals to reach the ears even though the composite transducer is in place over the ear canal. The attachment block 16 and 18 also serve as paths between the headband and the user's head to assist in the comfort factor of the headset. The adjustable headband is designed so that the wires crossing from one side of the user's head to the other are concealed reducing the risk of damage and aiding in cosmetic appearance. The boom microphone 22 is an optional feature that may be used for additional communication needs. Finally, the controller 28 is configured to allow several functions to be performed as will be described hereinafter.

The composite transducers 12 and 14 have for their purpose a solution of the problem of how to receive and convert the original acoustic wave signal to an electrical signal, process it with a 180 degrees phase shift, and convert it back to an acoustic signal so that it can add with the original acoustic wave signal and cancel out all in the real time domain. That is, the phase of all frequencies of the original acoustic wave are added substantially 180 degrees cut of phase to substantially cancel the original acoustic wave. The composite transducers 12 and 14 are identical in construction and therefore only one need be described in detail.

Figure 2B:
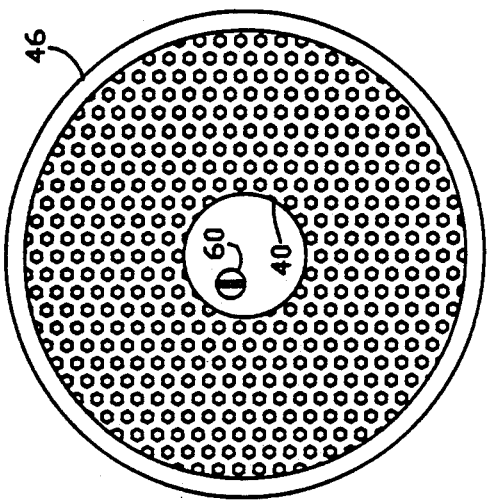
FIGS. 2a-2c are side, front and rear views respectively of the composite transducer.
Figure 2C:
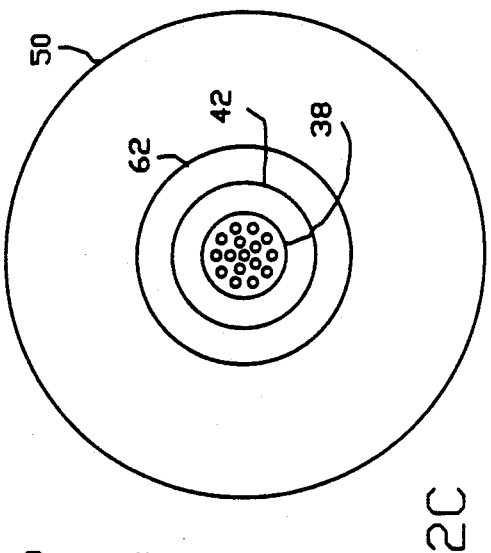
Figure 2A:
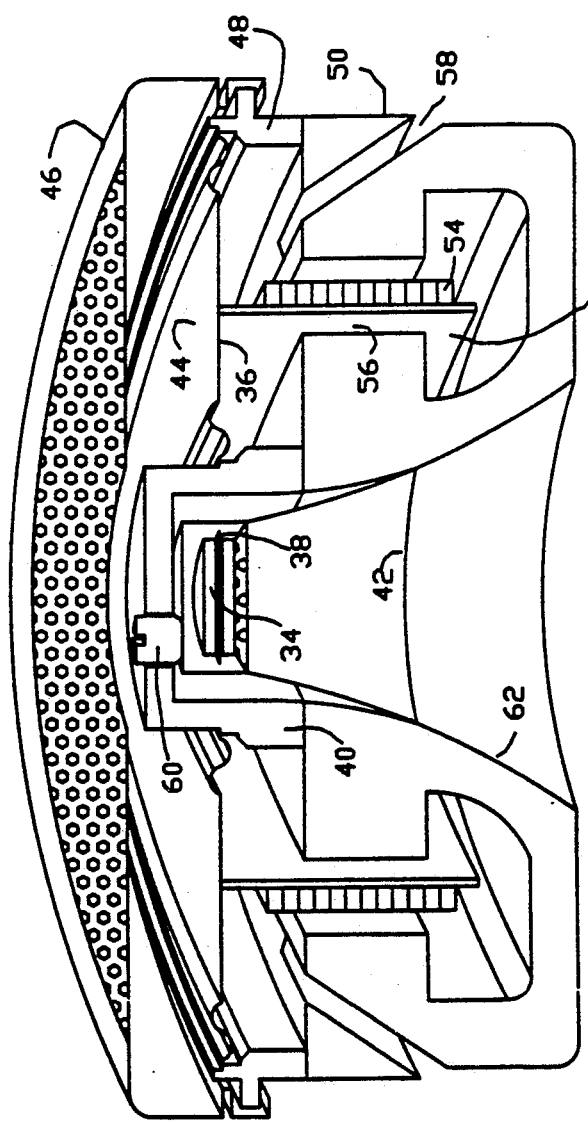

The composite transducer (FIGS. 2a-2c) includes an input transducer 34 (FIG. 2a) and an output transducer 36. The input transducer 34 is constructed of a material not influenced by a magnetic field. Thus, a suitable input transducer is an electret condenser or a piezoelectric element 38. An input transducer housing 42 and isolation cover 40 form an enclosure which contains a dead air space 41. This dead air space 41 serves to isolate the input transducer from the output transducer. Housing 42, isolation cover 40, and magnetic structure 50 also hold the input transducer 34 in place to provide additional isolation between the input transducer 34 and the output transducer 36 reducing the potential of feedback. An outer housing 46 covers the output transducer diaphragm 44. The output transducer 36 includes a diaphragm or cone 44 which is protected by a snap-on perforated cover 46. A mounting ring 48 holds the outer edge of the output transducer's diaphragm 44 and the snap-on cover 46. A magnet structure 50 is pinned to the mounting ring 48. A coil form 52 for coil windings 54 is attached to the output transducer's diaphragm 44 between its inner and outer peripheries. This coil form holds the winding centered in a gap 56 of the magnetic structure 50 and moves the output diaphragm 44 when a signal is applied to the coil. The output transducers magnetic structure 50 also provides the overstructure for the composite transducer. The magnetic structure has vent ports 58 spaced around the circumference of the structure to relieve back pressure to the output diaphragm 44. Thus, the output transducer 36 is fixed and the input transducer 34 and its housing 42 are moved by a set screw 60 to affect alignment of the input and output transducers diaphragms 38 and 44 in the same plane.

Thus, the composite transducer may be described as two independent transducers mounted so their diaphragms are oriented in opposite directions, with the input transducer mounted in the middle of the output transducer, and both diaphragms aligned in the same plane. The voice coil for the output transducer is mounted in the middle of the diaphragms which allows the pole piece to be hollowed to allow the mounting of the input transducer therein with its diaphragm in the same plane as the output diaphragm. The housing 40 covers this "hollow pole center" and the input transducer to prevent a direct feedback path between the diaphragms. The set screw 60 in this housing allows fine alignment of the input transducer's diaphragm with the output transducer's diaphragm.

The inside edges of this "hollowed pole center" has smooth conically expanding sides 62 to direct the acoustic signal source to the input diaphragm. This structure may be compared to a conical horn and is used to broaden the frequency range the input transducer can receive and to minimize the resonances and phase distortions caused by waveguides. It will be appreciated by those persons skilled in the art that other style waveguides, by their inherent properties, may be used to signature the received signal for individual applications.

The choice of transducer design is critical when constructing the composite transducer. As the output transducer is a voice coil type device, a magnetic field exists in the area that the input transducer occupies. If the input transducer were of a design similar to a dynamic microphone, the results would not be desirable. The magnetic field of the output transducer's section would interfere with the input section since the magnetic fields would be coupling and opposing in certain regions. Trying to share the same magnet structure for each transducer does not lend itself to aligning the diaphragms in the same plane with one inside the other. Thus, the design used for the input transducer should be of the electret microphone style, a piezo film transducer, or some other style and design that does not rely on a magnetic field that could be altered by the fields generated by the output transducer.

Accordingly, the above described composite transducer reduces to a negligible effect problems associated with the velocity of the acoustic wave, reflections or delays, and phase shift filters.

The control unit 28 (FIGS. 3a-3c) may be made small enough to fit into a pocket, or made to fit a variety of other size chassis. Thus, the in order that the controller may be worn on a belt, or clipped to apparel suitable to support the unit.

The front side 68 (FIG. 3b) of the controller 28 is provided with an access door 70 to a battery power pack compartment. Input transducer output gain adjusters 72 and 74 and a boom microphone gain adjuster 76 are provided on the front side above the access door for adjusting, respectively, the input transducer output gain and boom microphone gain.

The top side 78 (FIG. 3c) of the controller 28 is provided with 3 female type receptors 80, 82 and 84. Receptacle 80 is adapted to receive the mating plug 26 of the headset. The receptacles 82 and 84 are adapted to receive, respectively, a mating connector 86 for connecting an external power input, or an auxiliary signal input, or a boom microphone output, and a mating connector 88 for connecting a composite transducer input or composite transducer output, or a controller signal output.

Standard type gain adjusters 90, 92 and 94 are provided for adjusting, respectively, the headset gain, external input gain, and signal output gain of the left composite transducer 12; while, gain adjusters 96, 98 and 100 are provided for adjusting, respectively, the headset gain, external input gain and signal output gain of the right composite transducer 14.

Three toggle switches 102, 104 and 106 complete the configuration of the top of the controller 28. Toggle switch 102 is provided to control the headset functions and includes reduction, off and amplification positions; toggle switch 104 is provided to control the headset input and includes normal, off and external operation positions; and toggle switch 106 controls the power selection and includes battery, off and external positions.

Figure 4:
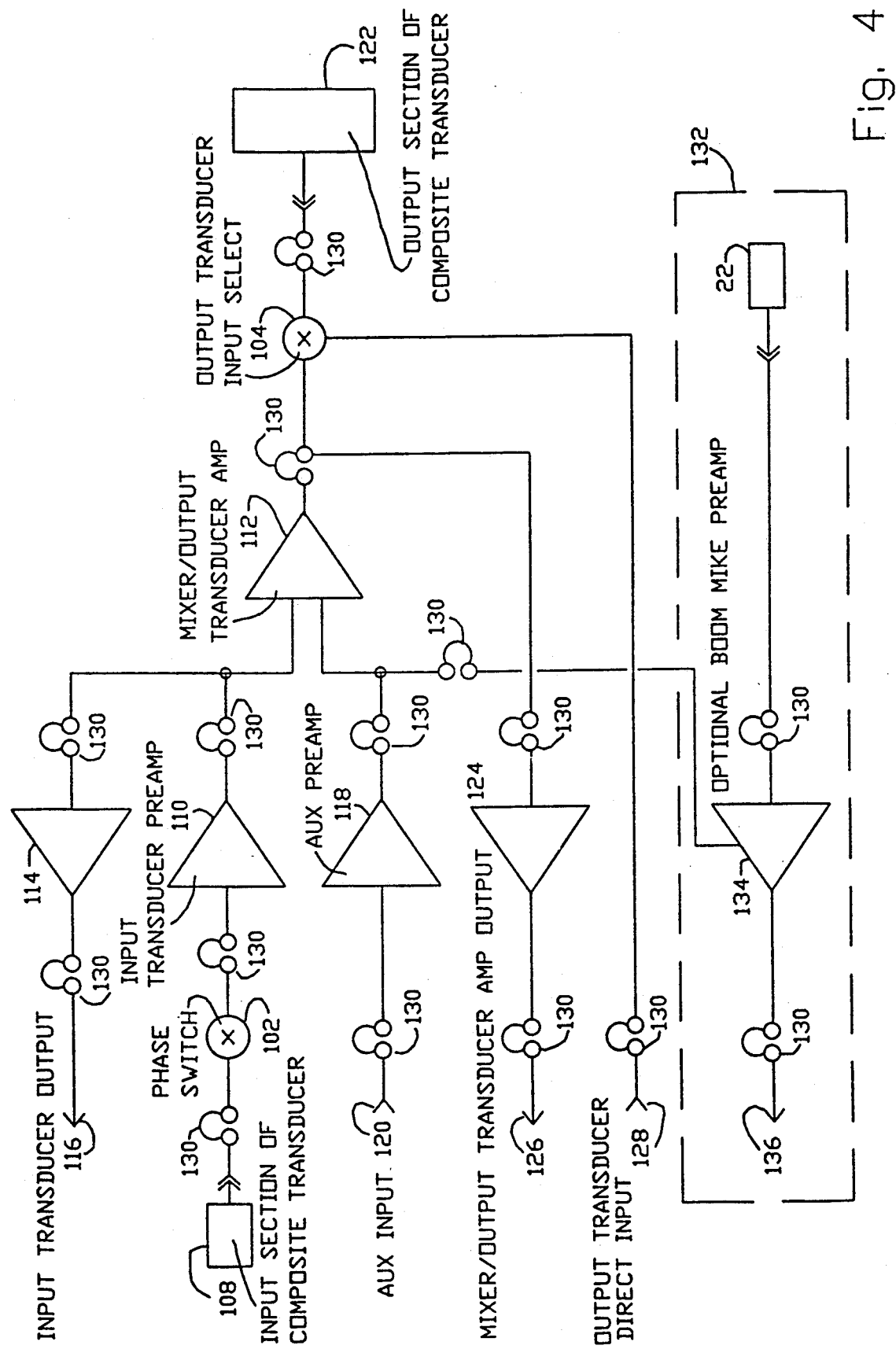
FIG. 4 is a schematic view in block form of the control circuitry.

Referring now to FIG. 4 for a description of the controller circuitry for one channel and the boom microphone circuit. The controller circuitry includes an input transducer section 108 of the composite transducer which converts the acoustic source signal to an electrical signal for processing. The headset function switch 102 is connected to the input section 108 to control the input transducer input to a transducer preamplifier 110. Switch 102 is a three-positioned switch used to select one of the following three functions:

1. The inverted phase for cancellation (reduction);
2. the normal phase for signal amplification; and
3. to cut off the input transducer.

The transducer preamplifier 110 is connected the junction of the inverted terminal of an operational amplifier (Op. Amp.) 112 serving as a mixer/output transducer amplifier and to an operational amplifier 114. Operational amplifier 114 has its output connected to an input transducer output connector 116. The noninverting terminal of the operational amplifier 112 is connected to the output of an auxiliary input instrumentation preamplifier 118 having its input terminal connected to an auxiliary input connector 120 for inputting a signal to the auxiliary input instrumentation preamp 118 to the Op. Amp. 112. The headset input switch 104 selects between the output of the mixer/output transducer (Op. Amp.) 112 or the output transducer direct input 128 for output to the output section of the composite transducer 122. The mixer/output transducer (Op. Amp.) 112 is buffered by (Op. Amp.) 124 for isolation and gain control to provide the controller generated signal to be output to connector 126.

An input connector 128 is connected to the switch 104 for inputting a signal to the transducer section 122. This input connector is used to allow the electroacoustic apparatus 10 to be used as a normal set of headphones.

The circuit is replete with patch points 130 for the addition of subcircuits or circuit components; for example, the transducer preamp 110 has a patch point for the addition of filters and/or phase shift circuits to provide a select narrow band noise cancellation if desired. Because of the design of the composite transducer, these circuits are not needed or used for broadband noise cancellation.

The optional boom microphone circuit 132 includes the boom microphone 22 which is connected by connector 26 to a preamplifier 134 for amplifying the signal output of the boom microphone to a working level. The Output of the optional boom mike preamp 134 is mixed with the output of the aux input preamp 118 and feed to the noninverting input of mixer/output transducer (Op. Amp.) 112. This provides a side tone signal to the operator of the signal from the boom microphone.

The operations of the electroacoustic apparatus 10, which is to provide each of the above mentioned useful tools for the ear and its hearing needs, are as follows:

1. For a device to reduce the sound level to the ears giving audible noise reduction the headset function switch 102 and the output transducer input section select switch are set, respectively, to the "Reduction" and "Normal" positions. Thus, an acoustic wave is detected and converted to electrical wave energy signals by the transducer input section 108 and fed to the phase selection switch 102. The switch 102, being positioned in the "Reduction" position, passes the electrical signals to an inverting input of the linear phase and gain instrumentation amplifier 110. After the signal has been inverted and amplified, it is fed to the mixer/amplifier (Op. Amp.) 112 that, in turn, delivers the amplified electrical signals to the selection switch 104 which being set to the "Normal" position passes the amplified electrical signals to the output transducer section 122.

The level that is outputted by the output section 122 of the composite transducer must be adjusted to match the level of the original signal in the ear canal. The individual level (gain) controls 90-94 and 96-100 are used to adjust the gain for the left and right ears, respectively. This is necessary because not everyone's ears are identical to each other or to anyone else's ear. Thus, maximum reduction is achieved by adjusting the gain until the signal heard by the ear has reached its minimum level and any more gain causes the signal to increase in gain.

2. For a device to perform a hearing aid function, such as amplifying the sound level to the ears, the apparatus can amplify a signal using two methods. The first method uses the exact same components and circuitry described above for use when reducing the signal level. The difference is that instead of adjusting the gain to maximize the reduction, the gain is increased beyond the point of minimum level heard by the ear to a desired level or the maximum level before feedback occurs between the input and output sections of the composite transducer. The second method uses the same components and circuitry except the phase or headset function switch 102 is set to the "Amplification" position. The difference in this setting is that the input transducer signal is not fed to the noninverting input of the instrumentation amplifier 102, and the gain of the system is adjusted to the desired level below feedback.

3. For a device to provide a communication interface for inputting special signals such as dispatched or emergency communications and providing a signal output from a boom microphone while using one of the desired functions of the apparatus such as its noise reduction capabilities, the apparatus will accept an external signal presented to the auxiliary input 120. This signal is fed to the Op. Amp. 118 to adjust the gain on the signal and to match impedances. The signal then goes to the mixer/output transducer amplifier 112 where it is summed with a signal presented by the input transducer amplifier 110. This summed signal is then passed to the output transducer input select or "Headset Input" switch 104. For boom microphone operation, the boom microphone 22 message signals are amplified by the preamplifier 134 and the resultant signal is presented to the output connector 136. An external device connected to the output connector 136 receives the resultant signal.

4. For an amplified headset device to be used with personal entertainment equipment or where other amplified signals are required to drive a miniature type headset, the headset function switch 102 is set to the "Off" position and the auxiliary input 120 is used. The "Off" setting of switch 102 prohibits any signal except the auxiliary input from being amplified and presented to the output transducer input select or "Headset Input" switch 104. The boom microphone would not normally be used in this mode of operation, but may be if needed to perform a special function such as an entertainer using the headset as a monitor and the boom microphone for singing or speaking.

5. For a signal source to feed personal or professional recording devices such as mono or binaural microphone sources, the apparatus will pass a signal from the input transducer sections 108 of the composite transducers mounted on the headset to the additional Op. Amp. 114 which isolates the output of the transducer preamp 110 from an input to a device such as a recorder that may be connected to the connector 116.

6. For a normal open air ultralight headphone for use in anyway that such a type headphone may be used, the output section 112 of the composite transducer is accessed directly by setting the output transducer input select or "Headset Input" switch 104 to its "External" position. This presents to the output transducers section 122 of the composite transducer the signal fed to the connector 128. Thus, except for the switch 104, no other internal circuitry is used.

Figure 5:
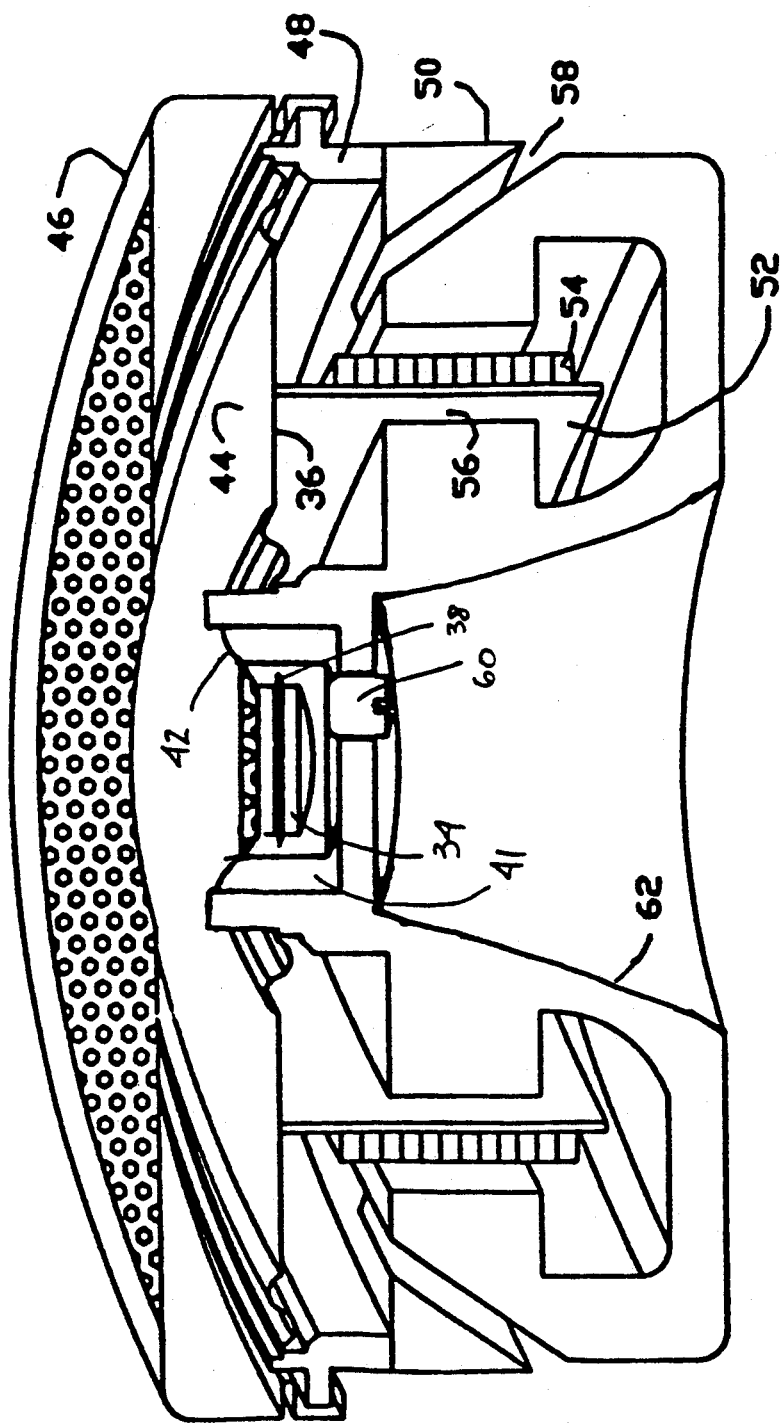
FIG. 5 is a side view of the second embodiment of the composite transducer.

FIG. 5 shows a second embodiment of the composite transducer. Parts of this second embodiment which correspond with parts of the previously described embodiment are denoted with like reference numerals. In the second embodiment, the input transducer and the output transducer face in the same direction. Accordingly, sound propagating from the diaphragm of the output transducer 44 propagates into the user's ear canal. Sound propagating in the opposite direction is received by the diaphragm of the input transducer 38. As in the previously described embodiment, both the input and output diaphragms are located in substantially the same plane. A set screw 60 is provided to fine tune the alignment of the input transducer into the plane of the output diaphragm.

Figure 6:
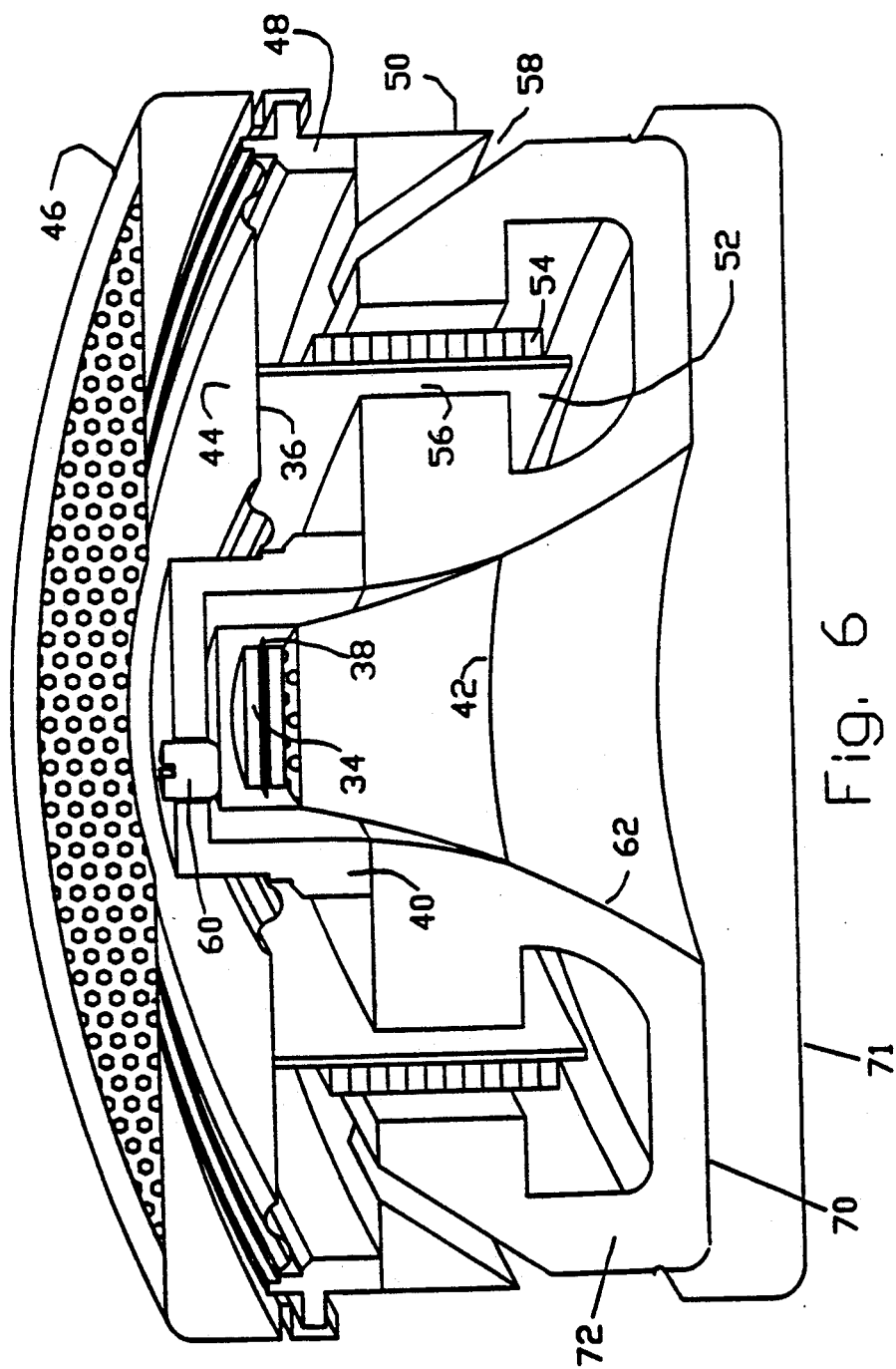
FIG. 6 is a side view of the composite transducer fitted with the isolation wall of the present invention.

FIG. 6 shows another feature of the present invention, the isolation wall means 71, which can be used with the first embodiment of the invention. This isolation wall means 71 is attached to the outer surface 70 of the frame 72 of the invention so that this isolation wall separates the vent ports 58 of the output transducer from the hollow pole center leading to the input transducer. This isolation wall means 71 therefore prevents sound propagating from the vent ports 58 from having a direct path into the hollow pole center. The isolation wall means may either be removably attached to frame 72 as shown in FIG. 6, or the isolation wall means 71 may be permanently attached to frame 72.

Although only two main embodiments of this invention have been described, it will apparent to a person skilled in the art that various modifications to the details of construction shown and described may be made without departing from the scope of this invention.

I claim:

1. An electroacoustic device for cancelling sound waves in a bounded ear canal, comprising:

an input transducer for converting sound waves incident on a pickup surface of the input transducer into corresponding input electrical signals;

an output transducer for converting output electrical signals into corresponding sound waves which emanate from a diaphragm surface of the output transducer into the bounded ear canal, said output transducer defining a boundary of the bounded ear canal;

a transducer frame to which said input transducer and said output transducer are fixed so that said pickup surface of said output transducer are in substantially the same plane, the input transducer and the output transducer being independently mounted on the transducer frame such that the movement of the pickup surface relative to the transducer frame is primarily in response to incident sound waves, said transducer frame defining another boundary of said bounded ear canal; and a control means for receiving the electrical signals from the input transducer and for generating the output electrical signals to the output transducer, the output electrical signals being substantially 180 degrees out of phase with respect to said sound waves incident on said pickup surface of said input transducer so that sound waves in said bounded ear canal are substantially cancelled;

said diaphragm of said output transducer being mounted to direct sound waves primarily toward said ear canal and said pickup device of said input transducer being mounted to face in the same direction relative to the ear canal when said device is mounted on a user's ear.

2. An electroacoustic device for cancelling sound waves in a bounded ear canal, comprising:

an input transducer for converting sound waves incident on a pickup surface of the input transducer into corresponding input electrical signals;

an output transducer for converting output electrical signals into corresponding sound waves which emanate from a diaphragm surface of the output transducer into said bounded ear canal, said output transducer defining a boundary of said bounded ear canal;

a transducer frame to which said input transducer and said output transducer are fixed so that said pickup surface of said input transducer and said diaphragm surface of said output transducer are in substantially the same plane, the input transducer and the output transducer being independently mounted on the transducer frame such that the movement of the pickup surface relative to the transducer frame is primarily in response to incident sound waves, said transducer frame defining another boundary of said bounded ear canal; and a control means for receiving the electrical signals from the input transducer and for generating the output electrical signals to the output transducer, the output electrical signals being substantially 180 degrees out of phase with respect to said sound waves incident on said pickup surface of said input transducer so that sound waves in said bounded ear canal are substantially cancelled;

said transducer frame including an inner surface for disposition adjacent a user's ear and an outer surface and wall means being mounted over said outer surface and carried by said transducer frame said wall means having a disc shaped wall portion, said outer surface having a selected surface area and said wall portion extending substantially coextensively with said outer surface to cover said surface area.

* * * * *